(12) United States Patent
Falk et al.

(10) Patent No.: US 8,496,952 B2
(45) Date of Patent: Jul. 30, 2013

(54) ANTIMICROBIAL COMPOSITIONS COMPRISING SILVER CHLORIDE AND BENZOISOTHIAZOLINE

(75) Inventors: Uwe Falk, Bruchkoebel (DE); Michael Marcus Walter, Liederbach (DE); Joerg Grohmann, Niedernhausen (DE)

(73) Assignee: Clariant Finance (BVI) Limited, Tortola (VG)

( * ) Notice: Subject to any disclaimer, the term of this patent is extended or adjusted under 35 U.S.C. 154(b) by 363 days.

(21) Appl. No.: 12/528,557

(22) PCT Filed: Feb. 20, 2008

(86) PCT No.: PCT/EP2008/001305
§ 371 (c)(1),
(2), (4) Date: Aug. 25, 2009

(87) PCT Pub. No.: WO2008/104310
PCT Pub. Date: Sep. 4, 2008

(65) Prior Publication Data
US 2010/0330142 A1 Dec. 30, 2010

(30) Foreign Application Priority Data

Feb. 27, 2007 (DE) .......................... 10 2007 009 450
Apr. 12, 2007 (DE) .......................... 10 2007 017 178

(51) Int. Cl.
*A01N 25/26* (2006.01)
*A01N 25/28* (2006.01)
*A01N 59/16* (2006.01)
*A61K 33/38* (2006.01)

(52) U.S. Cl.
USPC .......................................... 424/421; 424/618

(58) Field of Classification Search
USPC ................................. 424/421, 618
See application file for complete search history.

(56) References Cited

U.S. PATENT DOCUMENTS

| | | | |
|---|---|---|---|
| 4,150,026 A | 4/1979 | Miller et al. | |
| 4,906,466 A * | 3/1990 | Edwards et al. | 424/421 |
| 5,286,871 A | 2/1994 | Schmidt | |
| 5,364,649 A | 11/1994 | Rossmoore et al. | |
| 5,480,898 A | 1/1996 | Lindner | |
| 5,736,591 A | 4/1998 | Dunn | |
| 6,020,407 A * | 2/2000 | Campbell et al. | 524/156 |
| 6,355,752 B1 | 3/2002 | Brungs et al. | |
| 6,437,068 B2 | 8/2002 | Loffler et al. | |
| 6,444,726 B1 | 9/2002 | Brunt et al. | |
| 6,454,813 B1 | 9/2002 | Chan | |
| 6,461,386 B1 | 10/2002 | Chan et al. | |
| 6,641,829 B1 | 11/2003 | Green et al. | |
| 2005/0239358 A1 * | 10/2005 | Hanrahan et al. | 442/123 |
| 2008/0227766 A1 | 9/2008 | Wunder et al. | |

FOREIGN PATENT DOCUMENTS

| | | |
|---|---|---|
| EP | 0106562 | 4/1984 |
| EP | 0112610 | 7/1984 |
| EP | 0116865 | 8/1984 |
| EP | 0190504 | 8/1986 |
| EP | 0251783 | 1/1988 |
| EP | 0654470 | 5/1995 |
| EP | 0734651 | 10/1996 |
| EP | 0834253 | 4/1998 |
| EP | 1060142 | 9/1999 |
| EP | 1028129 | 8/2000 |
| EP | 1116733 | 7/2001 |
| EP | 1382248 | 1/2004 |
| EP | 1941797 | 7/2008 |
| FR | 2745579 | 9/1997 |
| GB | 1389940 | 4/1975 |
| JP | 08092019 | 4/1996 |
| JP | 11107162 | 4/1999 |
| JP | 2000026205 | 1/2000 |
| WO | WO 91/07395 | 5/1991 |
| WO | WO 99/44957 | 9/1999 |
| WO | WO 01/00021 | 1/2001 |
| WO | WO 2004/009055 | 1/2004 |
| WO | WO 2004/099308 | 11/2004 |
| WO | WO 2007/026004 | 3/2007 |
| WO | WO 2007/087326 | 8/2007 |

OTHER PUBLICATIONS

International Search Report for PCT/EP2008/001305, dated Apr. 21, 2009.
International Preliminary Examination Report for PCT/EP2008/001305, dated Sep. 1, 2009.
English abstract for JP59142543, Aug. 15, 1984, Konishiroku Photo Ind Co Ltd.
English abstract for JP2000026205, Jul. 9, 1998.
English abstract for JP11107162, Sep. 29, 1997.
English abstract for JP08092019, Sep. 27, 1994.

* cited by examiner

*Primary Examiner* — Fereydoun G Sajjadi
*Assistant Examiner* — Michael B Pallay
(74) *Attorney, Agent, or Firm* — Tod A. Waldrop

(57) ABSTRACT

The invention relates to a composition comprising a) silver and/or one or more silver compound and b) one or more biocidal active ingredients of the isothiazoline.

17 Claims, No Drawings

ANTIMICROBIAL COMPOSITIONS COMPRISING SILVER CHLORIDE AND BENZOISOTHIAZOLINE

The present invention relates to antimicrobial compositions comprising silver in the form of metallic silver or as silver compound(s) and at least one further biocidal active substance selected from the substance class of isothiazolines and their use as preservatives and disinfectants.

Biocides are used in highly diverse fields of application in order to control or to prevent the growth of microorganisms, and thus to ensure the preservation of products and materials. They are used in the building industry, textile industry, leather industry, paper industry, electronics industry and food industry, but also in cosmetics, and agriculture. Biocidal active substances are likewise used for preservation in paints and adhesives, water-in-oil emulsions and lubricants or for surface treatment. In order to achieve a broad activity spectrum of the preservatives against such various microorganisms as bacteria, fungi and molds, in most cases combination products of two or more biocidal active substances are used.

The antimicrobial effect of silver and silver salts has been known for a long time and is utilized for the antibacterial finishing of medical instruments and auxiliaries, but also for producing germ-resistant surfaces and textiles.

It is prior art to adsorb antimicrobially effective metals or metal compounds on a support material in order to achieve a slow release of silver or silver ions and attain a long-lasting antimicrobial effect.

In EP-A-0 116 865, metal compounds are applied to zeolites and introduced into polymers. EP-A-0 190 504 discloses antimicrobial compositions comprising metallic silver, adsorbed onto hydratable or hydrated oxides.

EP-A-0 251 783 and EP-A-0 734 651 describe silver compounds which are applied to water-insoluble, nonhydrated or -hydrolyzable oxides and exhibit a good bactericidal and fungicidal effect. According to U.S. Pat. Nos. 6,641,829, 6,461,386, 6,454,813 and 6,444,726, these supported silver compounds are used for the finishing of textiles with an antimicrobial active substance, for the preserving of cosmetics or else for the preserving of water-based polymer emulsions.

The silver-containing compositions cited in the prior art do not adequately fulfill a spontaneous and simultaneously a long-lasting antimicrobial effect in an environment which favors the growth of microorganisms and lose their effect in an aggressive environment. A further problem is the instability of silver compounds which, under the influence of light, leads to a darkening in the color of the products within minutes.

In order to achieve a broader activity spectrum, combination products of two or more biocidal active substances are required.

WO-A-01/00021 describes that the biocidal effect of pyrithione or of pyrithione complexes can be improved through silver salts, copper salts or zinc salts. AgCl and $Ag_2O$ are used in the specification. Data on the stability of the biocidal compositions, and also with regard to the color stability is not given.

EP-A-1 382 248 discloses that biocidal active ingredients from the group of haloalkynyls, for example 3-iodo-2-propynylcarbamate, decompose in the presence of metal ions, for example silver ions. This decomposition reaction can be reduced or prevented by adding amines. However, the presence of amines is undesired in many applications. Furthermore, aminic components, such as, for example, triazines, react with silver to give colored complexes and therefore cannot be used for many applications.

It has hitherto not been possible, to an adequate degree, to provide antimicrobial compositions which develop both an adequate spontaneous effect to prevent growth of microorganisms and at the same time are antimicrobially effective over long periods as a result of slow release of toxicologically and ecotoxicologically acceptable amounts of active substance(s).

In order to achieve the broadest possible activity spectrum of the antimicrobial compositions against such various microorganisms as bacteria, fungi, molds, algae and yeast, with good short-term and long-term effect, combination products of antimicrobial active substances are sought. Also required are antimicrobial compositions which, even at very low use concentrations, develop their effect spontaneously and lastingly, are toxicologically and ecotoxicologically acceptable and are color-stable over long periods.

It was therefore the object of the present invention to provide antimicrobial compositions which are effective against microorganisms from the group of bacteria, molds, algae and yeasts, are stable within a broad temperature range for long storage times, can be easily incorporated into formulations and products in very low concentrations, do not exhibit color changes in the end products, particularly under the influence of light, and are toxicologically and ecotoxicologically acceptable.

Surprisingly, it has now been found that silver in the form of metallic silver, silver compounds or silver or silver compounds adsorbed to support materials synergistically increases the bactericidal and fungicidal effect of isothiazolines, such that the use concentrations of both active substances can be reduced. The compositions comprising silver or one or more silver compound(s) on a support and at least one further antimicrobial active substance from the group of isothiazolines are characterized by high, spontaneous and also long-lasting efficiency against bacteria and fungi.

The invention therefore provides antimicrobial compositions comprising
 a) silver and/or one or more silver compound(s),
 b) one or more biocidal active substance(s) from the group of isothiazolines.

In accordance with the invention, metallic silver, preferably in the form of nanoparticles having particle sizes<100 nm, particularly preferably<50 nm, or else in the form of silver compounds are used. The silver compounds used are silver chloride, silver bromide, silver iodide, silver nitrate, $Ag_3PO_4$, $Ag_2SO_4$, $Ag_2CO_3$, silver citrate, silver stearate, silver acetate, silver lactate, silver salicylate, silver oxide (silver hydroxide), preferably silver chloride, silver citrate and silver nitrate.

In a preferred embodiment of the invention, the silver or the silver compound is adsorbed on a water-insoluble, inert, nonhydratable or nonhydrated, oxidic support material, and the silver and/or the silver compound(s), always calculated as elemental silver, are present, based on the weight of the support material, in amounts of from 0.1% by weight to 75% by weight.

The preferred support material is selected from titanium oxide, magnesium oxide, aluminum oxide, silicon oxide, calcium oxide and barium oxide, calcium hydroxyapatite, chalk, natural ground or precipitated calcium carbonates, calcium magnesium carbonates, silicates, sheet silicates, zeolites, clays or bentonites. The support material is particularly preferably titanium oxide which is present in one or more of the crystalline forms anatase, rutile and brookite. In likewise preferred embodiments, mixtures of the aforementioned support materials can be used.

The support material should have a particle size of less than 25 μm, preferably of <5 μm, particularly preferably <1 μm. In a further preferred embodiment, the support material has a particle size of <120 nm, particularly preferably <5 nm, in particular <25 nm.

The weight fraction of silver or of the silver compound, based on the weight of the support material, is in the range from 0.1% by weight to 75% by weight, preferably 5% by weight to 50% by weight, particularly preferably 10% by weight to 30% by weight, calculated as elemental silver.

The supported silver compounds used according to the invention are prepared in the manner described in EP-A-0 251 783 and are also available as commercial products (JMAC® LP 10, JMAC® Composite PG, Clariant Produkte (Deutschland) GmbH). Supported silver can be prepared from supported silver compounds by reducing the silver compounds to the metal.

Isothiazolines (which in the text below include their derivatives) are understood as meaning compounds according to formula (I) or (II)

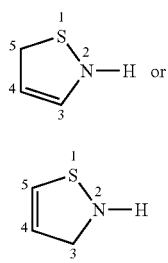

formula (I)

formula (II)

and derivatives thereof which can carry substituents at positions 2, 3, 4 and/or 5. Such substituents may, for example, be linear, branched or cyclic hydrocarbon groups, halogen atoms or carbonyl groups. Preferred hydrocarbon groups are $C_1$-$C_{12}$-alkyl groups, phenyl groups and condensed aromatic systems.

Further Preferred Derivatives of Isothiazoline are Isothiazolinones of Formula (III)

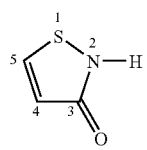

formula (III)

which can carry substituents like the isothiazolines described above.

Isothiazolines with biocidal effectiveness are, for example, nonhalogenated isothiazolines. Suitable nonhalogenated isothiazolines are, for example 2-methyl-3-isothiazoline, 2-methyl-4-isothiazolin-3-one, 2-ethyl-3-isothiazoline, 2-propyl-3-isothiazoline, 2-isopropyl-3-isothiazoline, 2-butyl-3-isothiazoline (in which butyl can be n-butyl, isobutyl or tert-butyl), 2-n-octyl-3-isothiazoline, 2-octyl-4-isothiazolin-3-one or 1,2-benzoisothiazolin-3-one or its alkali metal, alkaline earth metal or ammonium salt.

Isothiazolines with biocidal effectiveness are, for example, halogenated isothiazolines. Suitable halogenated isothiazolines are, for example, 5-chloro-2-methyl-3-isothiazoline, 5-chloro-2-methyl-4-isothiazolin-3-one or 4,5-dichloro-2-(n-octyl)-4-isothiazolin-3-one.

The preferred isothiazoline is 1,2-benzoisothiazolin-3-one according to formula (IV) and/or its alkali metal, alkaline earth metal or ammonium salt, in particular its sodium or potassium salt.

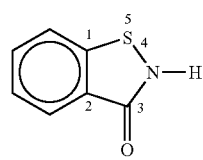

formula (IV)

The weight fraction of isothiazoline in the antimicrobial compositions according to the invention is 0.1% to 99%, preferably 1% to 50%, particularly preferably 2% to 20%, the weight fraction of silver or silver compound(s) is 0.01% to 50%, preferably 0.1% to 20%, particularly preferably 0.2% to 2%.

The weight ratio in which silver or the silver compound a) and the isothiazoline b) are present in the composition according to the invention is preferably a):b)=100:1 to 1:100, in particular a):b)=10:1 to 1:10, especially a):b)=3:1 to 1:3, for example a):b)=1:1 to 1:3. Here too, any silver compound which may be present is calculated as elemental silver.

The antimicrobial compositions according to the invention can be supplied in solid form as powders or as granules, or else in liquid form, preferably as aqueous dispersion, as emulsion or as suspoemulsion. The compositions are white to beige.

In a preferred embodiment, the antimicrobial compositions according to the invention are present in solid form as powders, granules or pellets.

The preparation of the antimicrobial compositions according to the invention in solid form can take place by mixing the two components isothiazoline and silver or silver compound or supported silver or silver compound, and optionally fillers and dispersants in customary mixing devices that operate batchwise or continuously and which are usually equipped with rotating mixing elements, for example in a plowshare mixer. Depending on the efficiency of the mixing device, the mixing times for a homogeneous mixture are generally between 30 seconds and 5 minutes.

The solid antimicrobial compositions according to the invention additionally optionally comprise fillers and dispersants.

Suitable fillers are titanium oxide, magnesium oxide, aluminum oxide, silicon oxide, calcium oxide and barium oxide, calcium hydroxyapatite, chalk, natural ground or precipitated calcium carbonates, calcium magnesium carbonates, silicates, sheet silicates, zeolites, clays or bentonites.

Suitable dispersants are the dispersants specified below, preference being given to polynaphthalenesulfonates, naphthalenesulfonates, alkylsulfosuccinates, in particular sodium dioctylsulfosuccinates.

In a further preferred embodiment, the antimicrobial compositions according to the invention are in the form of a dispersion, in particular on an aqueous basis.

The dispersions according to the invention are preferably prepared by dispersing isothiazoline, optionally with the addition of a dispersant, in water, and adding silver or one or more silver compounds or supported silver and/or a supported silver compound to the dispersion with stirring. Optionally, a further dispersant can also be added. In a further step, the dispersion can preferably be ground in a bead mill and the desired viscosity can be established using a thickener. It benzoisothiazoline is used in salt form, then it is advantageous to firstly prepare an aqueous dispersion of silver, silver compound or supported silver or silver compound, and to add the benzoisothiazoline salt to this.

Dispersants which can be used are nonionic, anionic and cationic dispersants.

Suitable dispersants are addition products of from 2 to 30 mol of ethylene oxide and/or up to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group; $C_{12}$-$C_{18}$-fatty acid mono- and diesters of addition products of from 1 to 30 mol of ethylene oxide onto glycerol; glycerol mono- and diesters and sorbitan mono- and diesters of saturated and unsaturated fatty acids having 6 to 22 carbon atoms and ethylene oxide addition products thereof; addition products of from 15 to 60 mol of ethylene oxide onto castor oil and/or hydrogenated castor oil; polyol, and in particular polyglycerol, esters, such as, for example, polyglycerol polyricinoleate and polyglycerol poly-12-hydroxystearate. Preferred liquid fatty acid esters are PEG-10 polyglyceryl-2 laurate and polyglyceryl-2 sesquiisostearate.

Also suitable are ethoxylated and nonethoxylated mono-, di- or trialkylphosphoric acid esters and alkylarylphosphoric acid esters, for example isotridecylphosphoric acid esters and salts thereof, tri-sec-butylphenolphosphoric acid esters and salts thereof and tristyrylphenylphosphoric acid esters and salts thereof.

Mixtures of compounds of two or more of these substance classes are likewise suitable. The addition products of ethylene oxide and/or propylene oxide onto fatty alcohols, fatty acids, alkylphenols, glycerol mono- and diesters, and sorbitan mono- and diesters of fatty acids or onto castor oil are known, commercially available products. These are homolog mixtures whose average degree of alkoxylation corresponds to the ratio of the quantitative amounts of ethylene oxide and/or propylene oxide and substrate with which the addition reaction is carried out.

Suitable cationic dispersants are, for example, di($C_{10}$-$C_{24}$)-alkyldimethylammonium chloride or bromide, preferably di($C_{12}$-$C_{18}$)-alkyldimethylammonium chloride or bromide; ($C_{10}$-$C_{24}$)-alkyldimethylethylammonium chloride or bromide; ($C_{10}$-$C_{24}$)-alkyl-trimethylammonium chloride or bromide, preferably cetyltrimethylammonium chloride or bromide and ($C_{20}$-$C_{22}$)-alkyltrimethylammonium chloride or bromide; ($C_{10}$-$C_{24}$)-alkyldimethylbenzylammonium chloride or bromide, preferably ($C_{12}$-$C_{18}$)-alkyl-dimethylbenzylammonium chloride; N—($C_{10}$-$C_{18}$)-alkylpyridinium chloride or bromide, preferably N—($C_{12}$-$C_{16}$)-alkylpyridinium chloride or bromide; N—($C_{10}$-$C_{18}$)-alkyl-isoquinolinium chloride, bromide or monoalkylsulfate; N—($C_{12}$-$C_{18}$)-alkylpolyoylamino-formylmethylpyridinium chloride; N—($C_{12}$-$C_{18}$)-alkyl-N-methylmorpholinium chloride, bromide or monoalkylsulfate; N—($C_{12}$-$C_{18}$)-alkyl-N-ethylmorpholinium chloride, bromide or monoalkylsulfate; ($C_{16}$-$C_{18}$)-alkylpentaoxyethylammonium chloride; diisobutylphenoxyethoxyethyldimethylbenzylammonium chloride; salts of N,N-diethyl-aminoethylstearylamide and -oleylamide with hydrochloric acid, acetic acid, lactic acid, citric acid, phosphoric acid; N-acylaminoethyl-N,N-diethyl-N-methylammonium chloride, bromide or monoalkylsulfate and N-acylaminoethyl-N,N-diethyl-N-benzyl-ammonium chloride, bromide or monoalkylsulfate, where acyl is preferably stearyl or oleyl.

In particularly preferred embodiments, polynaphthalenesulfonates, naphthalene-sulfonates, alkylsulfosuccinates, in particular dioctylsulfosuccinates, such as, for example sodium dioctylsulfosuccinate, are used. In the presence of these dispersants, a further increase in the antimicrobial effect is achieved according to the invention.

The antimicrobial compositions according to the invention can comprise 0.1 to 40% by weight, preferably 1 to 30% by weight, particularly preferably 3 to 20% by weight, of one or more emulsifiers or dispersants, based on the finished antimicrobial compositions.

The antimicrobial compositions according to the invention in the form of dispersions can comprise solvents. Suitable solvents are from the group of glycols, for example ethylene glycol, diethylene glycol, triethylene glycol, tetraethylene glycol, polyethylene glycol, propylene glycol, dipropylene glycol, tripropylene glycol, polypropylene glycol, polybutylene glycol, terminally capped glycols, for example monoethylene glycol dimethyl ether (monoglyme), diethylene glycol dimethyl ether (diglyme), triethylene glycol dimethyl ether (triglyme), triethylene glycol diethyl ether, tetraethylene glycol dimethyl ether and tetraethylene glycol diethyl ether, propylene glycol phenyl ether, polyethylene glycol dibutyl ether; polyethylene glycol diallyl ether; polyethylene glycol allyl methyl ether; polyalkylene glycols; polyalkylene glycol allyl methyl ether, alcohols, for example methanol, ethanol, n-propanol, isopropanol, n-butanol, isobutanol, t-butanol, n-pentanol, n-hexanol, 2-methoxyethanol, 2-butoxyethanol, 2-(2-butoxyethoxy)ethanol, phenoxyethanol, 2-(2-butoxyethoxyl)ethanol, 3-methoxybutanol, 1-methoxy-2-propanol, sec-butyl alcohol, tert-butyl alcohol, isobutyl alcohol, 2-ethylhexanol, 2-propoxyethanol, benzyl alcohol, phenethyl alcohol, 1,2,6-hexanetriol, alkanes, for example, pentane, hexane, heptane, chlorinated alkanes, for example methylene chloride, ethylene dichloride;

aromatics, for example benzene, toluene, xylene;

nitriles, for example acetonitrile;

amides, for example dimethylformamide, N,N-dimethylacetamide, hexamethyiphosphoramide;

ketones, for example acetone, ethyl methyl ketone, methyl isobutyl ketone, methyl isobutyl ketone, methyl amyl ketone, methyl isoamyl ketone, 2-butanone, ethers, for example isopropyl ether, acetates, for example ethyl acetate, propyl acetate, isopropyl acetate, butyl acetate, isobutyl acetate, 2-methoxyethyl acetate, 1-methoxy-2-propyl acetate, ethylene glycol diacetate, lactates, for example methyl lactate, ethyl lactate, phosphates, for example trihexyl(tetradecyl)phosphonium hexafluorophosphate, trihexyl(tetradecyl)phosphonium tetrafluorophosphate, amines, for example monoethanolamine, diethanolamine, triethanolamine, polyols, for example glycerol, trimethylolethane, trimethylolpropane, 1,3-propanediol, 1,4-butanediol, 1,6 hexanediol, and also tetrahydrofuran, 1,4-dioxane, dimethyl sulfoxide, diethyl carbonate, propylene carbonate, pyridine, picoline, lutidine, collidine, cyclohexanone and/or water.

According to the invention, the biocidal compositions can comprise up to 60% by weight, preferably 40 to 20% by weight, particularly preferably 15 to 5% by weight, of one or more of the abovementioned solvents.

In a preferred embodiment, besides silver in the form of metallic silver, a silver compound or supported silver or silver compound and at least one isothiazoline, the antimicrobial compositions according to the invention can comprise one or more further biocidal active substance(s).

Preferred further biocidal active substances are methylenebismorpholine, oxazolidine, 3-iodo-2-propynyl butylcarbamate, 2-bromo-2-nitropropanediol, glutaraldehyde, glutardialdehyde, sodium 2-pyridinethiol-1-oxide, p-hydroxybenzoic acid alkyl esters, tris(hydroxymethyl)nitromethane, dimethylol-dimethylhydantoin, 1,6-dihydroxy-2,5-dioxahexane; 1,2-dibromo-2,4-dicyanobutane; 3-(3,4-dichlorophenyl)-1,1-dimethylurea (diuron); N-cyclopropyl-N'-(1,1-dimethyl-ethyl)-6-(methylthio)-1,3,5-triazine-2,4-diamine; methyl benzimidazol-2-ylcarbamate (carbendazim); N-(1,1-dimethylethyl)-N'-ethyl-6-(methylthio)-1,3,5-triazine-2,4-diamine (terbutryn); 4-chloro-3,5-dimethylphenol; 2,4-dichloro-3,5-dimethylphenol; 2-benzyl-4-chlorophenol; 2,2'-dihydroxy-5,5'-dichlorodiphenylmethane; p-tertiary-amylphenol; o-phenylphenol; sodium o-phenyl-phenol; p-chloro-m-cresol; 2-(thiocyanomethylthio)benzothiazole; 3,4,4'-trichlorocarbanilide; 1-hydroxy-2-pyridinethione zinc; 1-(4-chlorophenyl)-4,4-dimethyl-3-(1H-1,2,4-triazol-1-ylmethyl)pentan-3-ole (tebuconazole), 1-[2-(2,4-dichlorophenyl)-4-propyl-1,3-dioxolan-2-ylmethyl)-1H-1,2,4-triazole (propiconazole), 3-iodo-2-propynyl butylcarbamate, 2-bromo-2-nitropropanediol, formaldehyde; urea; glyoxal; 2,2°-dithiobis(pyridine N-oxide), 3,4,4-trimethyloxazolidine, 4,4-dimethyloxazolidine, N-hydroxymethyl-N-methyldithiocarbamate, potassium salt, adamantane, N-trichloromethylthiophthalimide, 2,4,5,6-tetrachloroisophthalonitrile, 2,4,5-trichlorophenol, dehydroacetic acid, copper naphthenate, copper octoate, tributyltin oxide, zinc naphthenate, copper 8-quinolate.

Furthermore, biocides from the group of quaternary ammonium compounds are suitable, preferably alkyldimethylammonium chlorides, such as, for example, cocosdimethylammonium chloride, dialkyldimethylammonium chlorides, such as, for example, dicocosdimethylammonium chloride, alkyldimethylbenzylammonium chlorides, such as, for example, $C_{12/14}$-dimethylbenzylammonium chloride or cocosdimethyldichlorobenzylammonium chloride.

The antimicrobial compositions according to the invention can additionally comprise surfactants, thickeners, antigel agents, solubility promoters, low-temperature protectants, antifoams, buffers, wetting agents, complexing agents, sequestrants, electrolytes, extenders, fragrances and dyes.

In one embodiment, the antimicrobial compositions according to the invention can comprise anionic surfactants.

Preferred anionic surfactants are straight-chain and branched alkylsulfates, -sulfonates, -carboxylates, -phosphates, -sulfosuccinates and -taurates, alkyl ester sulfonates, arylalkylsulfonates and alkyl ether sulfates.

Alkylsulfates are water-soluble salts or acids of the formula $ROSO_3M$, in which R is preferably a $C_{10}$-$C_{24}$-hydrocarbon radical, particularly preferably an alkyl or hydroxyalkyl radical having 10 to 20 carbon atoms and particularly preferably a $C_{12}$-$C_{18}$-alkyl or hydroxyalkyl radical. M is hydrogen or a cation, preferably an alkali metal cation (e.g. sodium, potassium, lithium) or ammonium or substituted ammonium, e.g. a methyl-, dimethyl- and trimethylammonium cation or a quaternary ammonium cation, such as tetramethylammonium and dimethylpiperidinium cation and quaternary ammonium cations, derived from alkylamines, such as ethylamine, diethylamine, triethylamine and mixtures thereof.

The alkyl ether sulfates are water-soluble salts or acids of the formula $RO(A)_mSO_3M$, in which R is preferably an unsubstituted $C_{10}$-$C_{24}$-alkyl or hydroxyalkyl radical, particularly preferably a $C_{12}$-$C_{20}$-alkyl or hydroxyalkyl radical and especially preferably a $C_{12}$-$C_{18}$-alkyl or hydroxyalkyl radical. A is an ethoxy or propoxy unit, m is a number greater than 0, typically between 0.5 and 6, particularly preferably between 0.5 and 3, and M is a hydrogen atom or a cation, preferably a metal cation (e.g. sodium, potassium, lithium, calcium, magnesium), ammonium or a substituted ammonium cation. Examples of substituted ammonium cations are methyl-, dimethyl-, trimethylammonium- and quaternary ammonium cations, such as tetramethylammonium and dimethylpiperidinium cations, and also those which are derived from alkylamines, such as ethylamine, diethylamine, triethylamine or mixtures thereof. Examples which may be given are $C_{12}$-$C_{18}$-alkyl polyethoxylate (1.0)sulfate, $C_{12}$-$C_{18}$-alkyl polyethoxylate (2.25)sulfate, $C_{12}$-$C_{18}$-alkyl polyethoxylate (3.0)sulfate, $C_{12}$-$C_{18}$-alkyl polyethoxylate (4.0)sulfate, where the cation is sodium or potassium.

Likewise of suitability are alkylsulfonates having straight-chain or branched $C_6$-$C_{22}$-alkyl chains, for example primary paraffinsulfonates, secondary paraffinsulfonates, alkylarylsulfonates, for example linear alkylbenzenesulfonates having $C_5$-$C_{20}$-alkyl chains, alkylnaphthalenesulfonates, condensation products of naphthalenesulfonate and formaldehyde, lignosulfonate, alkyl ester sulfonates, i.e. sulfonated linear esters of $C_8$-$C_{20}$-carboxylic acids (i.e. fatty acids), $C_8$-$C_{24}$-olefinsulfonates, sulfonated polycarboxylic acids, prepared by sulfonation of the pyrolysis products of alkaline earth metal citrates.

Further suitable anionic surfactants are selected from alkyl glycerol sulfates, fatty acyl glycerol sulfates, oleyl glycerol sulfates, alkylphenol ether sulfates, alkylphosphates, alkyl ether phosphates, isethionates, such as acylisethionates, N-acyltaurides, alkylsuccinamates, sulfosuccinates, in particular dinonyl- or dioctyl-sulfosuccinates, monoesters of sulfosuccinates (particularly saturated and unsaturated $C_{12}$-$C_{18}$-monoesters) and diesters of sulfosuccinates (particularly saturated and unsaturated $C_{12}$-$C_{18}$-diesters), acyl sarcosinates, sulfates of alkyl polysaccharides, such as sulfates of alkyl polyglycosides, branched primary alkylsulfates and alkylpolyethoxycarboxylates, such as those of the formula $RO(CH_2CH_2O)_kCH_2COO^-M^+$, in which R is a $C_8$-$C_{22}$-alkyl group, k is number from 0 to 10 and M is a soluble, salt-forming cation.

Suitable nonionic surfactants are preferably fatty alcohol ethoxylates (alkyl polyethylene glycols), alkylphenol polyethylene glycols, alkyl mercaptan polyethylene glycols, fatty amine ethoxylates (alkyl amino polyethylene glycols), fatty acid ethoxylates (acylpolyethylene glycols), polypropylene glycol ethoxylates (e.g. Pluronics®), fatty acid alkylolamides (fatty acid amide polyethylene glycols), N-alkyl- and N-alkoxypolyhydroxy fatty acid amides, alkyl polysaccharides, sucrose esters, sorbitol esters and polyglycol ethers.

Suitable amphoteric surfactants are preferably amphoacetates, particularly preferably monocarboxylates and dicarboxylates, such as cocoamphocarboxypropionate, cocoamidocarboxypropionic acid, cocoamphocarboxyglycinate (or also referred to as cocoamphodiacetate) and cocoamphoacetate.

Suitable cationic surfactants are, for example, di-($C_{10}$-$C_{24}$)-alkyldimethylammonium chloride or bromide, preferably di-($C_{12}$-$C_{18}$)-alkyldimethylammonium chloride or bromide; ($C_{10}$-$C_{24}$)-alkyldimethylethylammonium chloride or bromide; ($C_{10}$-$C_{24}$)-alkyl-trimethylammonium chloride or bromide, preferably cetyltrimethylammonium chloride or bromide and ($C_{20}$-$C_{22}$)-alkyltrimethylammonium chloride or bromide; ($C_{10}$-$C_{24}$)-alkyldimethylbenzylammonium chloride or bromide, preferably ($C_{12}$-$C_{18}$)-alkyldimethylbenzylammonium chloride; N—($C_{10}$-$C_{18}$)-alkylpyridinium chloride or bromide, preferably N—($C_{12}$-$C_{16}$)-alkylpyridinium chloride or bromide; N—($C_{10}$-$C_{18}$)-alkylisoquinolinium chloride, bromide or monoalkylsulfate; N—($C_{12}$-$C_{18}$)-alkylpolyoylaminoformylmethylpyridinium chloride; N—($C_{12}$-$C_{18}$)-alkyl-N-methylmorpholinium chloride, bromide or monoalkylsulfate; N-($C_{12}$-$C_{18}$)-alkyl-N-ethyl-morpholinium chloride, bromide or monoalkylsulfate; ($C_{16}$-$C_{18}$)-alkylpentaoxyethyl-ammonium chloride; diisobutylphenoxyethoxyethyldimethylbenzylammonium chloride; salts of N,N-diethylaminoethylstearylamide and -oleylamide with hydrochloric acid, acetic acid, lactic acid, citric acid, phosphoric acid; N-acyl-aminoethyl-N,N-diethyl-N-methylammonium chloride, bromide or monoalkylsulfate and N-acylaminoethyl-N,N-diethyl-N-benzylammonium chloride, bromide or monoalkylsulfate, where acyl is preferably stearyl or oleyl.

The antimicrobial compositions according to the invention can comprise 0.1 to 40% by weight, preferably 1 to 30% by weight, particularly preferably 3 to 20% by weight, of one or more surfactants, based on the finished antimicrobial compositions.

The thickeners used are preferably carboxymethylcellulose and hydroxyethyl-cellulose, xanthan gum, guar guar, agar agar, alginates and tyloses, and also relatively high molecular weight polyethylene glycol mono- and diesters of fatty acids, hydrogenated castor oil, salts of long-chain fatty acids, for example sodium, potassium, aluminum, magnesium and titanium stearates or the sodium and/or potassium salts of behenic acid, but also polyacrylates, polyvinyl alcohol and polyvinylpyrrolidone, and also polysaccharides. Copolymers based on acryloyl-dimethyltauric acid, as described in EP-A-1 060 142, EP-A-1 028 129, EP-A-1 116 733, are likewise suitable.

The thickeners can be used in the antimicrobial compositions according to the invention preferably in amounts of from 0.01 to 5% by weight and in particular in amounts of from 0.5 to 2% by weight, based on the finished antimicrobial compositions.

Suitable solubility promoters are sodium toluenesulfonate, sodium cumenesulfonate, sodium xylenesulfonate, alkanephosfonic acids and alkenyldicarboxylic acids, and anhydrides thereof.

Substances which can function as low-temperature stabilizers are all those which are customarily used for this purpose. By way of example, mention may be made of urea, glycerol and propylene glycol. Hydrogen peroxide may be any inorganic peroxide which releases hydrogen peroxide in aqueous solution, such as, for example, sodium perborate (monohydrate and tetrahydrate) and sodium percarbonate.

Suitable antifoams are fatty acid alkyl ester alkoxylates; organopolysiloxanes such as polydimethylsiloxanes and mixtures thereof with microfine, optionally silanized, silica; paraffins; waxes and microcrystalline waxes and mixtures thereof with silanized silica. Mixtures of different foam inhibitors, for example those of silicone oil, paraffin oil and/or waxes, are also advantageous.

Suitable buffers are all customary acids and salts thereof. Preferably, mention may be made of phosphate buffers, carbonate buffers, citrate buffers.

Wetting agents that can be used are alcohol ethoxylates/propoxylates. Furthermore, the mixtures according to the invention preferably comprise neutralizing agents and extenders for adjusting the compositions to a viscosity of from 100 to 2000 mPa·s, preferably of about 600 mPa·s. Preferred extenders are inorganic salts, particularly preferably ammonium or metal salts, in particular of halides, oxides, carbonates, hydrogencarbonates, phosphates, sulfates and nitrates, in particular sodium chloride. Preferred neutralizing agents are NaOH and KOH.

As electrolyte, the antimicrobial compositions according to the invention can comprise inorganic and organic salts. Alkali metal, alkaline earth metal, metal or ammonium halides, nitrates, phosphates, carbonates, hydrogencarbonates, sulfates, silicates, acetates, oxides, citrates or polyphosphates are suitable. For example, $CaCl_2$, $MgCl_2$, LiCl, KCl, NaCl, $K_2SO_4$, $K_2CO_3$, $MgSO_4$, $Mg(NO_3)_2$, $ZnCl_2$, ZnO, MgO, $ZnSO_4$, $CuSO_4$, $Cu(NO_3)_2$ are preferably used.

In preferred embodiments, the antimicrobial compositions according to the invention comprise phosphates, in particular sodium hydrogenphosphate and sodium dihydrogenphosphate.

Suitable organic salts are ammonium or metal salts, preferably of glycolic acid, lactic acid, citric acid, tartaric acid, mandelic acid, salicylic acid, ascorbic acid, pyruvic acid, fumaric acid, retinoic acid, sulfonic acid, benzoic acid, kojic acid, fruit acid, maleic acid, gluconic acid, galacturonic acid. As electrolyte, the compositions can also comprise mixtures of different salts.

The antimicrobial compositions according to the invention can comprise electrolytes in amounts of from 0.01 to 50% by weight, preferably 0.1 to 20% by weight, particularly preferably 0.5 to 10% by weight, based on the antimicrobial compositions.

Suitable sequestrants are, for example, sodium tripolyphosphate (STPP), ethylenediaminetetraacetic acid (EDTA), salts thereof, nitrilotriacetic acid (NTA), polyacrylate, phosphonate, for example 1-hydroxyethane-1,1-diphosphonic acid (HEDP), salts of polyphosphoric acids, such as ethylenediaminetetramethylene-phosphonic acid (EDTMP) and diethylenetriaminepentamethylenephosphonic acid (DTPMP), oxalic acid, oxalic acid salt, citric acid, zeolite, carbonates and polycarbonates.

Suitable complexing agents are phosphonates, aminophosphonates and aminocarboxylates.

The antimicrobial compositions according to the invention are preferably used for preserving paints, coatings, printing inks, cooling lubricants, metalworking auxiliaries, crop protection formulations, construction chemicals and construction materials, such as sealants, jointing material and binders, and also adhesives and polymer emulsions.

The antimicrobial compositions according to the invention can be used directly or in dilution as disinfectants, particularly in the hygiene and sanitary sector. Even in very low concentrations, they have a disinfectant effect in detergents and cleaners, especially in detergents, in dishwashing detergents and in cleaners for hard surfaces, and also in cosmetic products, both in rinse-off and also in leave-on products.

Moreover, the antimicrobial compositions according to the invention can be incorporated into coating materials for surfaces, such as, for example, ceramic materials, plastics, wood, concrete, plaster, coating compositions or paints. Surfaces which are coated with such coating materials are thereby biocidally finished.

Furthermore, the antimicrobial compositions according to the invention are used in packaging materials, for example films, paper, in order to ensure that the materials are free from germs.

A further use of the antimicrobial compositions according to the invention is the antimicrobial finishing of textiles, leather, nonwoven materials and bandages.

The antimicrobial compositions according to the invention are used in amounts such that the treated substrate or the treated end product comprises 5-1000 ppm, preferably 10 to 600 ppm, particularly preferably 20 to 80 ppm, of biocidal active substances.

Formulations comprising the compositions according to the invention preferably have a pH of from 1 to 13.

Formulations comprising the compositions according to the invention, where the composition comprises isothiazoline and a water-soluble, nonsupported silver salt, preferably have a pH in the range from 5 to 13, preferably 7 to 12, particularly preferably 8 to 10.

Formulations comprising the compositions according to the invention, where the composition comprises isothiazoline and a supported silver compound, preferably have a pH in the range from 5 to 13, preferably 7 to 12, particularly preferably 8 to 10.

An essential feature of the invention is the synergistic effect of the combination of silver and/or silver compound and/or supported silver or silver compound and biocides from the group of isothiazolines, and also the good photostability of the compositions.

Furthermore, the increase in the biocidal effect of the compositions according to the invention in the presence of one or more additives, in particular of a dispersant, preferably of polynaphthalenesulfonate, naphthalenesulfonate, alkylsulfosuccinate, in particular sodium dioctylsulfosuccinate, is essential to the invention.

The biocidal effect of the antimicrobial compositions according to the invention is retained even under storage conditions in the temperature range of up to +50° C. and over several months. Discoloration of the products comprising the compositions according to the invention under the influence of light does not occur.

The spontaneous antimicrobial effect of the composition according to the invention comprising silver or one or more silver compound(s) and one or more isothiazoline(s) is significantly greater than that of the individual constituents, applied in identical concentrations. Whereas in the case of a contact time of about 2 hours with the combination products according to the invention virtually complete killing of microorganisms is achieved, this result cannot be achieved either with the silver compounds or with the isothiazolines on their own.

A further surprising advantage of the invention is the exceptional color stability of the compositions comprising silver or silver compound and one or more isothiazoline(s).

The compositions according to the invention are stable at low and high temperatures and under the influence of light over several months and can be supplied in solid form or else in combination with a suitable medium, for example water, liquid hydrocarbons, for example ethanol or isopropanol, preferably as dispersions.

EXAMPLES

The examples below serve to illustrate the invention in more detail. Unless stated otherwise, all of the percentages are percentages by weight.

The following biocide compositions were used:
Composition 1
AgCl on $TiO_2$, 10% strength dispersion with 10% sodium dioctylsulfosuccinate
Composition 2
AgCl on $TiO_2$, 100% solids
Composition 3
AgCl on $TiO_2$, diluted with $TiO_2$, 100% strength solids
Composition 4
Benzoisothiazoline, about 75% strength
Composition 5
Benzoisothiazoline, 20% strength dispersion
Composition 6
Benzoisothiazoline, 33% strength dispersion
Composition 7
Benzoisothiazoline, 9.5% strength solution Example 1

Rate of the Antimicrobial Effect of Ag Salt/BIT (kill-kinetic measurement according to the Clariant method) of the composition Ag/BIT in comparison to the individual biocides AgCl, $AgNO_3$, composition 1 and composition 5

Reagents:
0.1 M phosphate buffer

| a) | $Na_2HPO_4 \, 7H_2O$ | 53.65 g in 1000 ml of water |
|---|---|---|
| b) | $NaH_2PO_4 \, 2H_2O$ | 18.07 g in 500 ml of water |

900 ml of phosphate buffer pH 7.0:
600 ml of $H_2O$ dest. +117 ml of (b)+183 ml of (a)
Bacteria:

| *Staphylococcus aureus* | DSM 799 | eq.: NCTC 10788 |
|---|---|---|
| *Pseudomonas aeruginosa* | DSM 1128 | eq.: NCIMB 8026 |
| *E-Coli* | DSM 682 | eq.: NCIMB 8545 |
| *Enterobacter aerogenes* | NCIMB 10102 | |

The bacteria are cultivated on a caso agar.
Sample 1
Description of the kill-kinetic measurement according to the Clariant method After the bacteria have spent 24 hours on the culture medium (caso agar), 10 ml of the 0.1 M phosphate buffer are added thereto and mixed for 20 seconds using a vortex mixer; 9 ml of the 0.1 M buffer solution are added to 1 ml of this solution; in turn, 1 ml of this solution are taken and 9 ml of 0.1 M phosphate buffer are added. The resulting solution is the inoculum with which the test series is carried out.

| Sample 1: | 19 ml of 0.1 M phosphate buffer + 1 ml of inoculum |
|---|---|
| Sample 2: | Sample 1 + 80 ppm of (Ag + BIT, 1:1) + 500 ppm sodium dioctylsulfosuccinate |
| Sample 3: | Sample 1 + 80 ppm of (Ag + BIT, 1:1) |
| Sample 4: | Sample 1 + 80 ppm of (Ag + BIT, 1:2) |
| Sample 5: | Sample 1 + 80 ppm of (Ag + BIT, 2:1) |
| Sample 6: | Sample 1 + 80 ppm of composition 2 |
| Sample 7: | Sample 1 + 80 ppm of composition 5 |
| Sample 8: | Sample 1 + $AgNO_3$ (80 ppm of Ag) |
| Sample 9: | Sample 1 + AgCl (80 ppm of Ag) |
| Sample 10: | Sample 1 + 80 ppm of (Ag + BIT, 10:1) |

-continued

Sample 11:   Sample 1 + 80 ppm of (Ag + BIT, 100:1)
Sample 12:   Sample 1 + 80 ppm of (Ag + BIT, 1:10)
Sample 13:   Sample 1 + 80 ppm of (Ag + BIT, 1:100)

The concentration data given for the above samples refer in each case to elemental silver and pure BIT (i.e. not in salt form). Thus, for example in sample 4, $AgNO_3$ and BIT were mixed together such that the mixture comprised 26.7 ppm of Ag, calculated as element, and 53.3 ppm of BIT, calculated as pure substance.

The germ count was determined in each case at the start (0 h), after 0.5 h, 1 h; 2 h; 3 h; 5 h; 7 h and 24 h in accordance with the TVC method European Pharmacopoeia 2.6.12.

TABLE 1

Germ counts as a function of time

| Sample | 0 | 0.5 | 1 | 2 | 3 | 5 | 7 | 24 h |
|---|---|---|---|---|---|---|---|---|
| 1 | 2.2U+07 | 2.0U+07 | 2.2U+07 | 2.0U+07 | 4.0U+07 | 1.0U+08 | 1.0U+08 | >1.0U+08 |
| 2 | 2.2U+07 | 1.8U+05 | 1.8U+04 | 1.0U+01 | 1.0U+01 | 1.0U+01 | 1.0U+01 | <10 |
| 3 | 2.2U+07 | 4.0U+06 | 1.4U+06 | 3.4U+05 | 2.0U+04 | 5.6U+03 | 3.7U+02 | <10 |
| 4 | 2.2U+07 | 3.6U+06 | 2.8U+06 | 1.4U+03 | 2.7U+02 | 5.0U+01 | 1.0U+01 | <10 |
| 5 | 2.2U+07 | 4.0U+06 | 3.2U+06 | 7.0U+05 | 4.8U+04 | 3.0U+04 | 4.0U+03 | <10 |
| 6 | 1.4U+06 | 6.0U+05 | 4.8U+05 | 2.0U+05 | 1.0U+05 | 8.0U+04 | 8.0U+04 | 2.8U+02 |
| 7 | 1.4U+06 | 5.6U+05 | 5.0U+05 | 3.6U+05 | 3.6U+05 | 3.6U+05 | 3.2U+05 | 4.0U+03 |
| 8 | 1.4U+06 | 4.0U+05 | 3.7U+05 | 1.4U+05 | 7.0U+04 | 4.0U+04 | 2.4U+02 | |
| 9 | 1.4U+06 | 8.0U+05 | 4.0U+05 | 2.0U+05 | 1.2U+05 | 8.0U+04 | 5.2U+04 | 1.0U+02 |
| 10 | 1.6U+06 | 6.0U+05 | 6.0U+04 | 6.8U+04 | 2.2U+04 | 6.0U+03 | 6.0U+03 | 1.7U+02 |
| 11 | 1.6U+06 | 6.4U+05 | 4.0U+05 | 1.0U+05 | 3.4U+04 | 4.4U+03 | 2.2U+03 | <10 |
| 12 | 1.6U+06 | 3.2U+05 | 2.4U+04 | 1.0U+01 | 1.0U+01 | 1.0U+01 | 1.0U+01 | <10 |
| 13 | 1.6U+06 | 3.6U+05 | 2.0U+05 | 3.2U+03 | 6.0U+01 | 1.0U+01 | 1.0U+01 | <10 | e.g. $2.2\ U+07 = 2.2 \cdot 10^7$

Benzoisothiazoline (sample 7) on its own only develops its antimicrobial effect after many hours; the efficiency of the silver ions (sample 8 and 9) is moderate in the first few hours. The combination of the two active substances Ag and BIT leads to a synergistic effect which comes into play after a contact time of just 1 to 2 hours on the microorganisms. A further significant increase in the effectiveness is achieved by adding the dispersant sodium dioctylsulfosuccinate (sample 2).

Example 2

Rate of the Antimicrobial Effect of Supported Silver/BIT (Kill-kinetic measurement according to the Clariant method) of silver-BIT mixtures in comparison to the individual biocides silver and BIT Reagents:

0.1 M phosphate buffer

| a) | $Na_2HPO_4\ 7H_2O$ | 53.65 g in 1000 ml of water |
| b) | $NaH_2PO_4\ 2H_2O$ | 18.07 g in 500 ml of water |

900 ml of phosphate buffer pH 7.0:

600 ml of $H_2O$ dest. +117 ml of (b)+183 ml of (a)

Bacteria:

| *Staphylococcus aureus* | DSM 799 | eq.: NCTC 10788 |
| *Pseudomonas aeruginosa* | DSM 1128 | eq.: NCIMB 8026 |
| *E-Coli* | DSM 682 | eq.: NCIMB 8545 |
| *Enterobacter aerogenes* | NCIMB 10102 | |

The bacteria are cultivated on a caso agar.

Sample 1

After the bacteria have spent 24 hours on the culture medium (caso agar), 10 ml of the 0.1 M phosphate buffer are added thereto and mixed for 20 seconds using a vortex mixer; 9 ml of the 0.1 M buffer solution are added to 1 ml of this solution; in turn, 1 ml of this solution are taken and 9 ml of 0.1 M phosphate buffer are added. The resulting solution is the inoculum with which the test series is carried out.

| Sample 1: | 19 ml of 0.1 M phosphate buffer + 1 ml of inoculum |
| Sample 2: | Sample 1 + 40 ppm of composition 1 + 40 ppm |

Composition 5

| Sample 3: | Sample 1 + 60 ppm of composition 1 + 20 ppm |

Composition 5

| Sample 4: | Sample 1 + 20 ppm of composition 1 + 60 ppm |

Composition 5

| Sample 5: | Sample 1 + 80 ppm of composition 1 |
| Sample 6: | Sample 1 + 40 ppm of composition 1 |
| Sample 7: | Sample 1 + 80 ppm of composition 5 |

The germ count was determined in each case at the start (0 h), after 0.5 h, 1 h; 2 h; 3 h; 5 h; 7 h and 24 h in accordance with the TVC method European Pharmacopoeia 2.6.12.

TABLE 2

Germ counts as a function of time

| Sample | 0 h | 0.5 h | 1 h | 2 h | 3 h | 5 h | 7 h | 24 h |
|---|---|---|---|---|---|---|---|---|
| 1 | 2.0U+06 | 1.6U+06 | 1.6U+06 | 2.4U+06 | 1.0U+07 | 2.4U+07 | 5.2U+07 | >1.0U+8 |
| 2 | 1.8U+06 | 1.2U+05 | 1.6U+03 | 1.0U+01 | 1.0U+01 | 1.0U+01 | 1.0U+01 | <10 |
| 3 | 1.8U+06 | 2.4U+05 | 2.0U+04 | 1.0U+03 | 4.8U+02 | 1.0U+01 | 1.0U+01 | <10 |
| 4 | 1.8U+06 | 1.2U+05 | 6.0U+03 | 1.0U+01 | 1.0U+01 | 1.0U+01 | 1.0U+01 | <10 |
| 5 | 2.0U+06 | 8.0U+05 | 4.8U+05 | 8.0U+03 | 2.4U+04 | 6.0U+2 | 1.0U+01 | <10 |
| 6 | 2.0U+06 | 6.0U+05 | 3.2U+05 | 8.0U+04 | 6.0U+04 | 1.4U+04 | 4.0U+02 | <10 |
| 7 | 1.8U+06 | 1.6U+06 | 1.8U+06 | 8.0U+05 | 6.0U+05 | 6.6U+05 | 4.2U+05 | <10 |

Benzoisothiazoline on its own only develops its antimicrobial effect after many hours; the efficiency of the silver ions is moderate in the first few hours. The combination of the two active substances silver and BIT leads to a synergistic effect, which comes into play after a contact time of just 1 to 2 hours on the microorganisms.

TABLE 3

Color stability of Ag/BIT compared with AgCl, AgNO$_3$, JMAC

| Product | Appearance after: | | | | | | |
|---|---|---|---|---|---|---|---|
| | immediately | 5 min | 30 min | 1 h | 2 h | 6 h | 24 h |
| AgCl | white | gray | dark gray | dark gray | dark gray | dark gray | dark gray |
| Support-bonded AgCl | pale gray | pale gray | gray | dark gray | dark gray | dark gray | dark gray |
| Support-bonded AgCl + BIT | pale beige | pale beige | pale beige | beige pale gray | beige pale gray | beige pale gray | beige pale gray |
| AgNO$_3$ solution | gray | dark gray | dark gray | dark gray | dark gray | dark gray | dark gray |
| AgNO$_3$ + BIT 100:1 | gray-tinged | pale gray | gray | gray | dark gray | dark gray | dark gray |
| AgNO$_3$ + BIT 10:1 | white | gray-tinged | pale gray | gray | gray | gray | dark gray |
| AgNO$_3$ + BIT 2:1 | white | pale beige | pale beige | pale beige | beige | beige | beige |
| AgNO$_3$ + BIT 1:1 | white | pale beige | pale beige | pale beige | pale beige | pale beige | pale beige |
| AgNO$_3$ + BIT 1:2 | white | white | white | white | white | white | pale beige |
| AgNO$_3$ + BIT 1:10 | white | white | white | white | white | white | pale beige |
| AgNO$_3$ + BIT 1:100 | white | white | white | white | white | white | pale beige |

TABLE 4 pH dependence of the silver-BIT
Silver nitrate was initially introduced and BIT was added in the ratio 1:2. This mixture initially had a pH of 10.
The batch was divided and the samples were adjusted to the pH values given below using nitric acid or sodium hydroxide solution:

| pH | Color (after 2 weeks)** | Size of the particles | Volume % after settling | Sedimentation speed |
|---|---|---|---|---|
| 2 | red-brown | large flakes | 45% | a few minutes |
| 4 | pale brown-gray | large flakes | 70% | a few minutes |
| 6 | pale yellow | large flakes | 90% | a few minutes |
| 7 | white | small flakes | 15% | one hour |
| 8 | white | very fine particles | 15% | 6 hours |
| 10 | white | very fine particles | 8% | 24 hours* |
| 13 | white | very fine particles | 15% | one hour |

*After 24 hours, more than 90% of the precipitate had settled, but a slight white shimmer still remained in the water phase for 3 to 4 days.
**The color changes in the acidic pH range occurred within the first 24 hours, and did not change further afterwards.

Formulation Examples

Example 3

10.0% composition 1
45.0% composition 5
0.4% xanthan gum
44.6% water

Preparation

Initially introduce composition 5 into water, add an aqueous dispersion of composition 1 with stirring (Ultra Turrax), grind in a bead mill and adjust the viscosity using xanthan gum.

Example 4

20.0% composition 1 (0.4% silver compound as active substance)
9.1% composition 6 (3% active substance)
0.4% xanthan gum
70.5% water Preparation Initially introduce composition 6 into water, add composition 1 with stirring (Ultra Turrax), grind in a bead mill and adjust the viscosity using xanthan gum.

Example 5

30.0% composition 1 (0.6% silver compound as active substance)
10.5% composition 7 (1% active substance)
0.4% xanthan gum
59.1% water Preparation Initially introduce composition 7, disperse composition 1 in water and, with stirring, add to the solution of composition 7 (Ultra Turrax) and adjust the viscosity using xanthan gum.

Example 6

1.0% composition 2
15.0% composition 5

1.5% dioctylsulfosuccinate
0.4% xanthan gum
82.1% water
Preparation

Initially introduce dioctylsulfosuccinate into water, add composition 5 and composition 1 with stirring (Ultra Turrax), grind in a bead mill and adjust the viscosity using xanthan gum.

Example 7

3.0% composition 2
2.7% composition 4
2.0% dioctylsulfosuccinate
0.4% xanthan gum
91.1% water
Preparation Initially introduce dioctylsulfosuccinate into water and, using an Ultra Turrax, firstly disperse composition 4 then composition 2, grind in the bead mill and adjust the viscosity using xanthan gum.

Example 8

10.0% composition 3
15.0% composition 4
1.5% polynaphthalenesulfonate
0.4% xanthan gum
82.1% water
Preparation Initially introduce polynaphthalenesulfonate into water and, using an Ultra Turrax, disperse firstly composition 4 then composition 3, grind in the bead mill and adjust the viscosity using xanthan gum.

Example 9

10.0% composition 1
15.0% composition 5
1.0% polynaphthalenesulfonate
1.5% dioctylsulfosuccinate
0.4% xanthan gum
72.1% water
Preparation Initially introduce polynaphthalenesulfonate and dioctylsulfosuccinate into water and, using an Ultra Turrax, disperse firstly composition 5 then composition 1, grind in the bead mill and adjust the viscosity using xanthan gum.

Example 10

10.0% composition 3
4.0% composition 4
0.5% polynaphthalenesulfonate
85.5% titanium dioxide

Example 11

10.0% composition 3
4.0% composition 40.5% polynaphthalenesulfonate
1.0% sodium dihydrogenphosphate
84.5% titanium dioxide

Example 12

20.0% composition 1
9.1% composition 6
2.0% disodium hydrogenphosphate/sodium dihydrogenphosphate 3:1
0.4% xanthan gum
68.5% water

The invention claimed is:

1. A composition comprising
a) silver chloride, and
b) benzoisothiazoline or a salt thereof,
wherein the silver chloride is adsorbed on a water-insoluble, inert, nonhydratable or nonhydrated, oxidic support, and the silver chloride, calculated as elemental silver, based on the weight of the support, is present in amounts of from 0.01% by weight to 75% by weight.

2. The composition as claimed in claim 1, wherein the water-insoluble, inert, nonhydratable or nonhydrated, oxidic support is selected from the group consisting of titanium oxide, magnesium oxide, aluminum oxide, silicon oxide, calcium oxide, barium oxide, calcium hydroxyapatite, chalk, natural ground or precipitated calcium carbonates, calcium magnesium carbonates, silicates, sheet silicates, zeolites, clays, bentonites and titanium oxide.

3. The composition as claimed in claim 1, wherein the weight fraction of benzoisothiazoline is 0.1% to 90%.

4. The composition as claimed in claim 1, wherein the weight fraction of silver chloride, calculated as elemental silver, is 0.01% to 50%.

5. The composition as claimed claim 1, comprising 0.1% by weight to 90% by weight, of benzoisothiazoline and 0.01% by weight to 50% by weight of silver chloride, calculated as elemental silver.

6. The composition as claimed in claim 1, wherein the weight ratio of constituent a), calculated as elemental silver, to constituent b) is in the range from 1:100 to 100:1.

7. The composition as claimed in claim 1, wherein the weight ratio of constituent a), calculated as elemental silver, to constituent b) is in the range from 1:10 to 10:1.

8. The composition as claimed in claim 1, wherein the weight ratio of constituent a), calculated as elemental silver, to constituent b), is in the range from 1:1 to 1:3.

9. The composition as claimed in claim 1, wherein the support material has a particle size of less than 25 μm.

10. The composition as claimed in claim 1, wherein the weight fraction of silver chloride, calculated as elemental silver, based on the weight of the support material, is in the range from 1% by weight to 50% by weight.

11. The composition as claimed in claim 1, further comprising 0.1 to 40% by weight of polynaphthalenesulfonate, naphthalenesulfonate or alkyl sulfosuccinate.

12. The composition as claimed in claim 1, wherein the weight fraction of benzoisothiazoline is 1% to 50%.

13. The composition as claimed in claim 1, wherein-the weight fraction of benzoisothiazoline is 2% to 20%.

14. The composition as claimed in claim 1, wherein the weight fraction of silver chloride, calculated as elemental silver, is 0.1% to 20%.

15. The composition as claimed in claim 1, wherein the weight fraction of silver chloride, calculated as elemental silver, is 0.2% to 2%.

16. The composition as claimed in claim 1, wherein the weight fraction of silver chloride, calculated as elemental silver, based on the weight of the support material, is in the range from 10% by weight to 30% by weight.

17. A process for antimicrobially treating a substrate, comprising the step of contacting the substrate with a composition as claimed in claim 1, wherein the treated substrate comprises an amount of from 5 to 1,000 ppm of the composition as claimed in claim 1.

* * * * *